US00PP34759P2

(12) United States Plant Patent
Van Swieten

(10) Patent No.: US PP34,759 P2
(45) Date of Patent: Nov. 22, 2022

(54) ***PHALAENOPSIS* ORCHID PLANT NAMED 'PHA731834'**

(50) Latin Name: ***Phalaenopsis* hybrid**
Varietal Denomination: 'PHA731834'

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 37 days.

(21) Appl. No.: 17/803,308

(22) Filed: Apr. 28, 2022

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — Jondle & Associates, P.C.

(57) ABSTRACT

A new and distinct variety of *Phalaenopsis* plant named 'PHA731834', particularly characterized by having reddish-purple, striped flowers with small white edges and dark purplish-red lips, flowers that are concave in lateral view, dark purplish-red whiskers with white tips, and is propagated by meristem tissue culture, is disclosed.

3 Drawing Sheets

Genus and species: *Phalaenopsis* hybrid.
Variety denomination: 'PHA731834'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA731834'.

The new *Phalaenopsis* plant is a product of a planned breeding program conducted by the inventor in Bleiswijk, the Netherlands. The objective of this breeding program was to create a new *Phalaenopsis* plant with attractive, reddish-purple, striped flowers with small white edges and dark purplish-red lips, suitable for potted plant production.

The new *Phalaenopsis* plant 'PHA731834' is a result of cross-pollination made by the inventor in April 2011 in Bleiswijk, the Netherlands, of the proprietary female, or seed parent, *Phalaenopsis* hybrid '01-3358' (unpatented) with the proprietary male, or pollen parent, *Phalaenopsis* hybrid '26514-01' (unpatented).

The new *Phalaenopsis* was selected by the inventor as a single plant within the progeny of the stated cross-pollination in a controlled greenhouse in Bleiswijk, the Netherlands, in June 2014. Asexual reproduction of the new *Phalaenopsis* plant by meristem tissue culture since 2017 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Apr. 22, 2021 (Application no. 2021/1092), by Applicant who obtained the subject matter disclosed directly from the inventor. 'PHA731834' has not been made publicly available or sold anywhere in the world prior to the effective filing date of this application with the exception of sales or disclosures made one year or less before the effective filing date of this claimed invention by Applicant who obtained 'PHA731834' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA731834' as a new and distinct variety of *Phalaenopsis* plant:

1) Reddish-purple, striped flowers with small white edges and dark purplish-red lips;
2) Flower shape in lateral view is concave; and
3) Whiskers are dark purplish-red with white tips.

DESCRIPTION OF THE PHOTOGRAPHS

This new *Phalaenopsis* plant is illustrated by the accompanying photographs which show the overall plant habit including blooms, bud, and foliage of the plant; the colors shown are as true as can be reasonably obtained by conventional photographic procedures. The photographs were taken in a greenhouse in Bleiswijk, the Netherlands, from 50-week-old plants in March 2022. Colors in the photographs may differ from the color values cited in the detailed botanical description, which accurately describe the actual colors of the new variety.

DESCRIPTION OF THE NEW VARIETY

Figure 1:
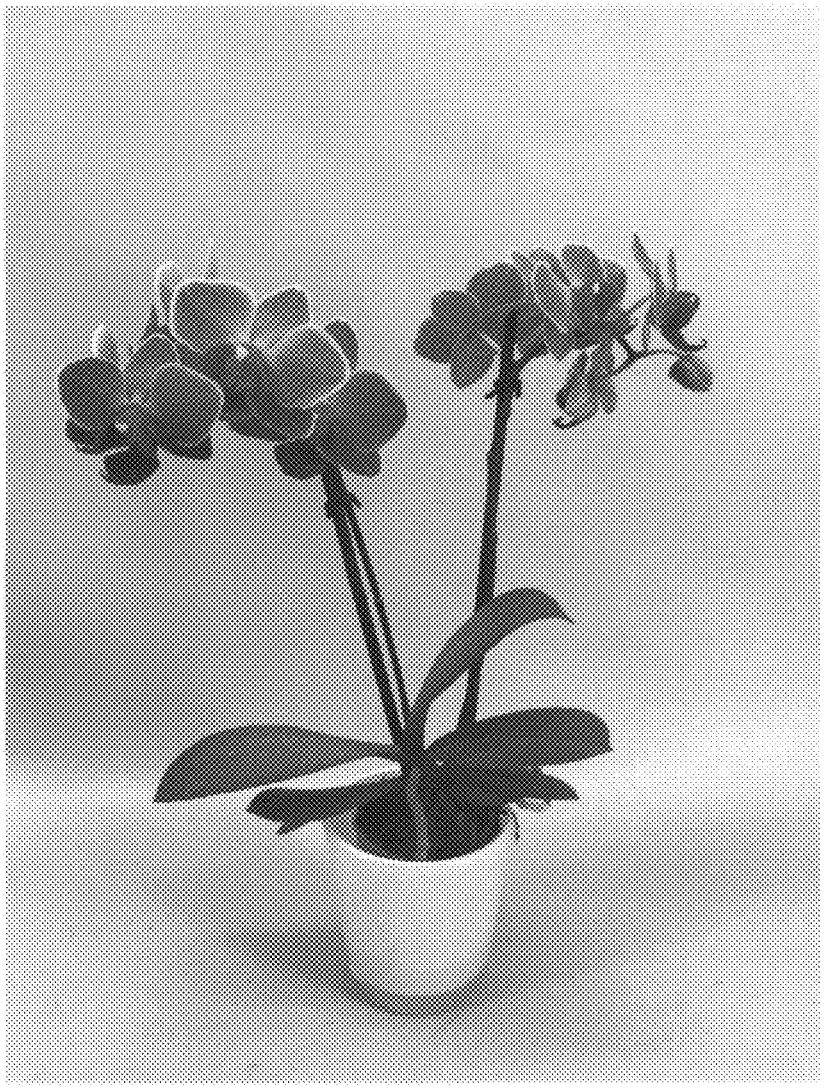
FIG. 1 shows the overall plant habit, including blooms, bud, and foliage of 'PHA731834'.
Figure 2:
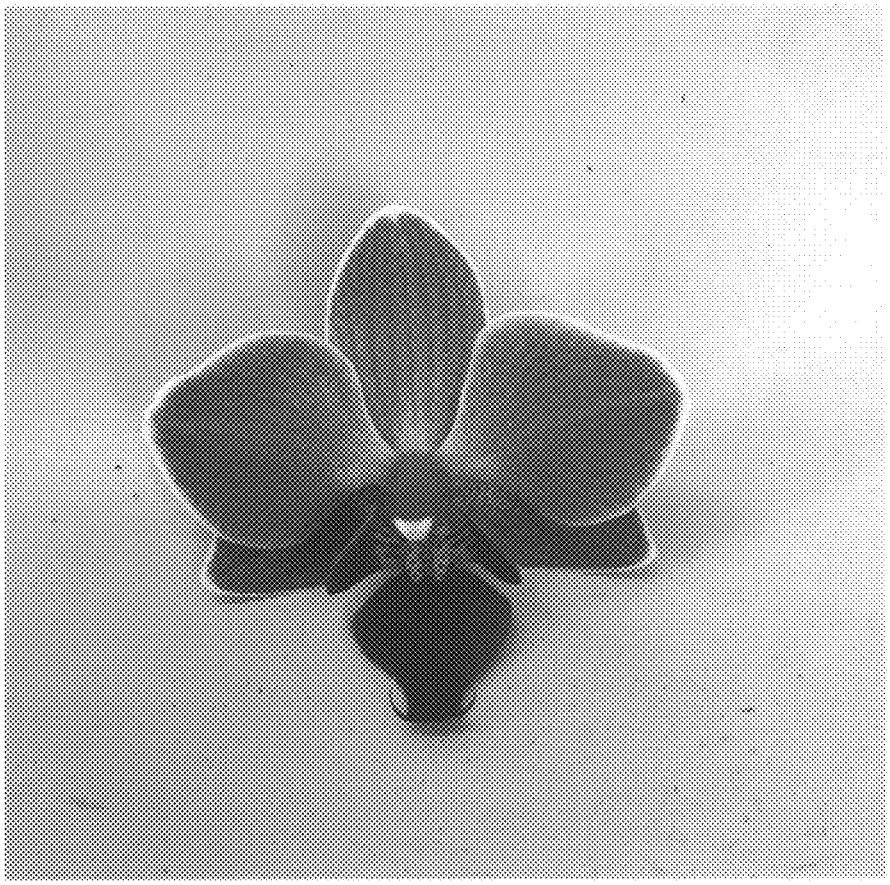
FIG. 2 shows a close-up of a flower of 'PHA731834'.
Figure 3:
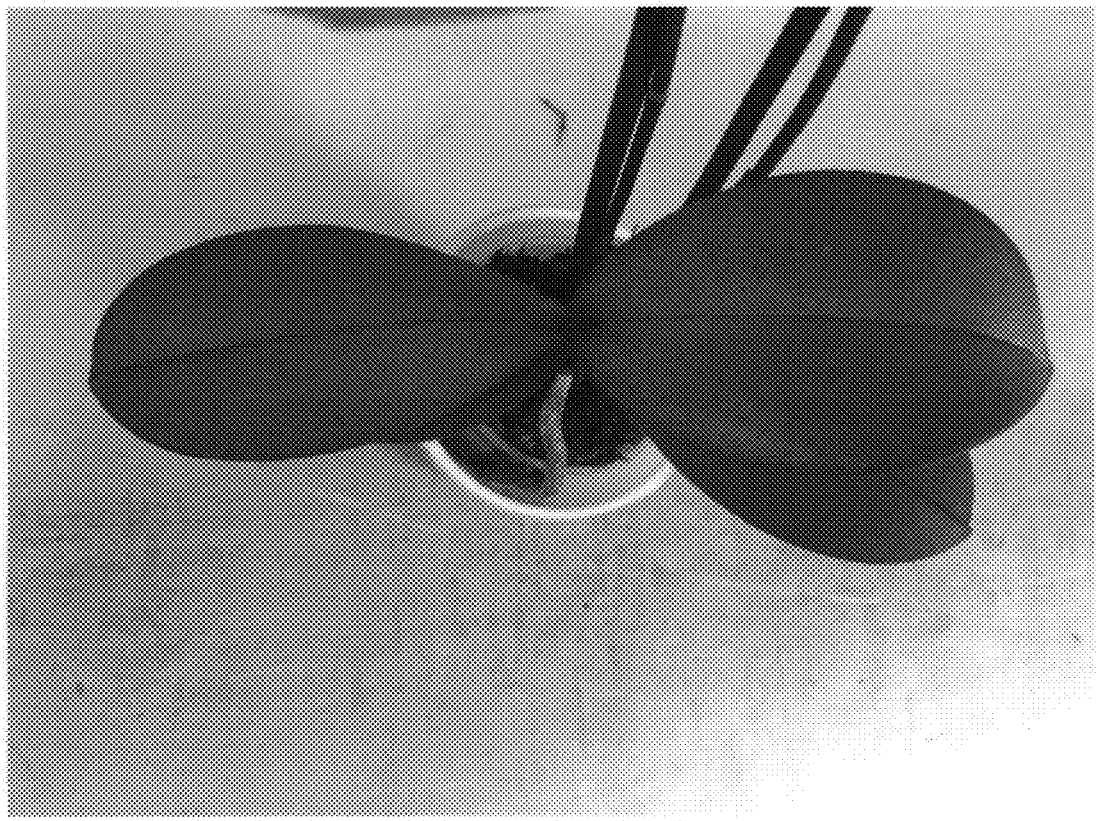
FIG. 3 shows an overhead view of the leaves of 'PHA731834'.

The following detailed description sets forth the distinctive characteristics of 'PHA731834'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in March 2022 on flowering plants which were planted in 6-centimeter (diameter) pots. After in vitro propagation, the plants were directly transplanted into 6-centimeter (diameter) pots and grown in a greenhouse between 27° C. to 29° C. for 32 weeks, continued by a cooling period of 6 weeks between 18° C. to 20° C. and 12 weeks in a greenhouse of 21° C. Flowering occurs after 50 weeks in 6-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHA731834'.

Parentage:

*Female parent*.—*Phalaenopsis* cultivar '01-3358' (unpatented).

*Male parent*.—*Phalaenopsis* cultivar '26514-01' (unpatented).

Propagation:

*Type*.—Meristem tissue culture.

Roots:

*Root description*.—Greyed-green (a color in between RHS 190B and RHS 190C) colored roots with branching lateral roots having yellow-green (RHS 144B) with a small purple (RHS N77A) colored root tips.

Plant:

*Crop time to flowering*.—Following asexual propagation (in vitro), the plant is directly transplanted into a 6-cm pot and the plant is finished after 48 to 50 weeks.

*Growth habit of the peduncle*.—Upright to slightly pendent with raceme inflorescence.

*Height (from soil level to top of inflorescence)*.—Approximately 21.0 cm to 26.0 cm.

*Width (measured from leaf tips)*.—About 16.0 cm to 19.0 cm.

*Vigor*.—Strong.

Leaves:

*Mature leaves*.—Quantity per plant: 6 to 8 leaves are produced before flowering. Length (fully expanded): 9.0 cm to 11.0 cm. Width: 4.0 cm to 5.0 cm. Position of the broadest part of the leaf: At the middle. Shape: Oblong. Base shape: Moderately elongated. Apex: Obtuse asymmetric. Leaf blade angle with the petiole (measured from the horizontal position): Between 15 degrees and 30 degrees. Leaf margin: Entire. Color: Upper surface: Yellow-green (RHS 146A) with small dark purplish-red dots (RHS N79A). Lower surface: Yellow-green (RHS 146B) with purple shade and small dots (RHS N77A). Texture (both upper and lower surfaces): Smooth. Thickness: 2.0 mm to 3.0 mm. Variegation: Absent. Venation: Pattern: Parallel. Color of the midvein: Upper surface: Yellow-green (RHS 146A) with a touch of dark purplish-red (RHS N79B). Lower surface: Yellow-green (RHS 146B) with a touch of dark purplish-red (RHS N79C).

Peduncle:

*Quantity per plant*.—1 to 3.

*Number of flowers per peduncle*.—6 to 9.

*Length*.—21.0 cm to 26.0 cm.

*Diameter*.—2.0 mm to 3.0 mm.

*Strength*.—Strong.

*Aspect*.—Upright to slightly pendent.

*Texture*.—Smooth.

*Color*.—Mix of purple (RHS N77A) and yellow-green (RHS 146B).

*Internode length*.—1.5 cm to 2.0 cm.

Inflorescence description:

*Appearance*.—Upright to slightly pendent, raceme inflorescence with bilaterally symmetrical flowers that open in succession beginning with the lowermost flower.

*Number of inflorescences*.—1 to 3.

*Inflorescence size*.—Height (from base to tip): 60.0 mm to 100.0 mm.

*Flowering time*.—First flowers can be expected 8 to 9 months after planting in a 6-cm pot.

*Flower*.—Height: 40.0 mm to 45.0 mm. Diameter: 50.0 mm to 55.0 mm. Depth of lip: 17.0 mm to 19.0 mm.

*Flower shape*.—Concave.

*Flower longevity*.—On the plant: 11 to 13 weeks.

*Fragrance*.—Absent.

*Flower bud*.—Average size: Medium. Length: 16.0 mm to 18.0 mm. Width: 14.0 mm to 16.0 mm. Shape: Egg shaped. Color: Touch of yellow-green (RHS 146D) at the base; purplish-red shade (RHS N77B) and dark purplish-red stripes (RHS N79B).

*Petals*.—Arrangement: Open/free. Shape: Semi-circular. Apex: Slightly emarginated asymmetric. Margin: Weakly undulated. Length (from base to tip): 23.0 mm to 25.0 mm. Width: 23.0 mm to 25.0 mm. Position of the broadest part of the petal: Toward the base. Color (when fully opened): Upper surface: Basic color: Reddish-purple (a color in between RHS N78A and RHS N78B). Over color: Purplish-pink (RHS N78C); reddish-purple stripes (RHS N78A); white edge (RHS NN155C). Lower surface: Basic color: Purple (RHS N80B). Over color: Reddish-purple stripes (RHS N78B). Number of spots and stripes on the petals (upper surface): Many stripes. Color of spots and stripes on the petals (upper surface): RHS N78A. Density of netting of the petals (upper surface): None. Color of the netting (upper surface): None.

*Dorsal sepal*.—Shape: Elliptic. Apex: Emarginated symmetric. Margin: Entire. Length (from base to tip): 25.0 mm to 27.0 mm. Width: 15.0 mm to 17.0 mm. Position of the broadest part of the dorsal sepals: Toward the base. Color (when fully opened): Upper surface: Basic color: Reddish-purple (RHS N78B). Over color: Reddish-purple stripes (RHS N78B); small white edge (RHS NN155C). Lower surface: Basic color: Purplish-pink (RHS N78C). Over color: Reddish-purple (RHS N78B) at the base; stripes (RHS N78A); a small white edge (RHS NN155C). Number of spots and stripes on the dorsal sepals (upper surface): Many stripes. Color of spots and stripes on the dorsal sepals (upper surface): RHS N78A. Density of netting of the dorsal sepals (upper surface): Low. Color of the netting: RHS N78A.

*Lateral sepals*.—Shape: Ovate. Apex: Obtuse asymmetric. Margin: Entire. Length (from base to tip): 25.0 mm to 27.0 mm. Width: 16.0 mm to 18.0 mm. Position of the broadest part of the lateral sepals: Toward the base. Color (when fully opened): Upper surface: Basic color: Reddish-purple (RHS N78B). Over color: Hint of light yellow-green (RHS 145C); purplish-red spotted (RHS 59B) at the base; reddish-purple stripes (RHS N78A). Lower surface: Basic color: Purplish-pink (RHS N78C). Over color: Touch of light yellow-green (RHS 145D) at the base; reddish-purple stripes (RHS N78B) and reddish-purple midvein (RHS N78A). Number of spots and stripes on the lateral sepals (upper surface): Few spots at the base and medium stripes. Color of spots and stripes on the lateral sepals (upper surface): Spots (RHS 59B) and stripes (RHS N78A). Density of netting of the lateral sepals (upper surface): Absent. Color of the netting (upper surface): Not applicable.

*Labellum* (*lip*).—Whiskers: Present. Length of whiskers: 3.0 mm to 4.0 mm. Color of whiskers: Dark purplish-red (RHS N79C) with white tips (RHS NN155C). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Undulated (widely wavy). Length: 14.0 mm to 16.0 mm. Width: 9.0 mm to 11.0 mm. Color: Upper surface: Hint of light yellow (RHS 8D) with dark red stripes (RHS 187C) at the base; red-purple (a color in between RHS N78A and RHS N79C) toward the tip with dark red overcolor (RHS 187B). Lower surface: Light yellow-green (RHS 155A) at the base toward one side and red (RHS 185A) toward the other side; dark reddish-purple (RHS N79C) toward the tip with dark red overcolor (a color in between RHS 187B and RHS 187C). Number of spots and stripes on the lateral lobe: Few stripes. Color of spots and stripes on the lateral lobe: RHS 187C. Density of netting of the lateral lobe: None. Color of the netting: None.

*Apical lobe*.—Shape: Trullate to rhombic. Margin: Entire. Length: 17.0 mm to 19.0 mm. Width: 16.0 mm to 18.0 mm. Color: Upper surface: Purplish-red (RHS 187D) with dark red overcolor (RHS 187C). Lower surface: Yellowish-white (RHS 196D) at the middle from the base toward whiskers; purplish-red wings (RHS 71A) and purplish-red margins of wings (RHS 59B); red-purple (a color in between RHS N78A and RHS N79C) toward wings. Number of spots and stripes on the apical lobe: None. Color of spots and stripes on the apical lobe: Not applicable. Density of netting of the apical lobe: None. Color of the netting: None.

*Callus*.—Average size: Small. Height: 4.0 mm to 5.0 mm. Length: 4.0 mm to 5.0 mm. Width: 3.0 mm to 4.0 mm. Color: Yellow (RHS 12A); spotted (RHS N186D); light greenish-yellow on sides (RHS 4C).

Reproductive organs:

*Column*.—Length: 7.0 mm to 9.0 mm. Diameter: 4.0 nun to 5.0 mm. Color: Reddish-purple (RHS N78A).

*Pollinia*.—Quantity: 2. Diameter: 0.9 mm to 1.1 mm. Color: Orange-yellow (RHS 23A).

*Ovary*.—Length: 9.0 mm to 11.0 mm. Diameter: 1.5 mm to 1.9 mm.

*Pedicel*.—Length: 29.0 nun to 31.0 mm. Diameter: 2.0 mm to 2.4 mm. Color: Hint of light yellow-green (RHS 196C) at the base and light reddish-purple (RHS N78D) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA731834' differs from the female parent plant '01-3358' (unpatented) in that 'PHA731834' has trullate to rhombic apical lobes, flowers with a main color of reddish-purple, and dark purplish-red whiskers with white tips, whereas '01-3358' has triangular apical lobes, flowers with a main color of light purple, and purplish-pink whiskers with white tips.

'PHA731834' differs from the male parent plant '26514-01' (unpatented) in that 'PHA731834' has dark purplish-red whiskers with white tips and calluses with a main color of yellow, whereas '26514-01' has reddish-purple whiskers with small white tips and calluses with a main color of light yellow-green.

'PHA731834' is most similar to the commercial *Phalaenopsis* plants named 'PHALFEMYM' (U.S. Plant Pat. No. 29,783) and 'PHALFUFLY' (U.S. Plant Pat. No. 31,024). 'PHA731834' differs from the commercial variety 'PHALFEMYM' in that 'PHA731834' has trullate to rhombic apical lobes and obtuse leaf apexes, whereas 'PHALFEMYM' has ovate apical lobes and rounded leaf apexes. Additionally, 'PHA731834' has longer dorsal sepals than 'PHALFEMYM'.

'PHA731834' differs from the commercial variety 'PHALFUFLY' in that 'PHA731834' has trullate to rhombic apical lobes and whiskers, whereas 'PHALFUFLY' has ovate apical lobes and no whiskers. Additionally, 'PHA731834' has longer dorsal sepals than 'PHALFUFLY'.

I claim:

1. A new and distinct variety of *Phalaenopsis* plant named 'PHA731834', substantially as described and illustrated herein.

* * * * *